United States Patent [19]

Katz et al.

[11] 3,940,317

[45] Feb. 24, 1976

[54] METHOD OF ISOLATION OF LYSOZYME

[76] Inventors: Friedrich D. Katz, 96-08 70th Ave., New York, N.Y. 11375; Louis Fishman, 143 N. Grove St., Valley Stream, N.Y. 11580; Milton Levy, 39-95 48th St., New York, N.Y. 11104

[22] Filed: Apr. 6, 1973

[21] Appl. No.: 348,780

[30] Foreign Application Priority Data
Feb. 26, 1973 Germany............................ 2309440

[52] U.S. Cl............................................. 195/66 R
[51] Int. Cl.$^2$ C07G 7/02; C07G 7/022; C07G 7/026
[58] Field of Search .................................. 195/66 R

[56] References Cited
OTHER PUBLICATIONS

Pryme et al., Biochemical and Biophysical Research Communications, Vol. 36, No. 4, 1969, pp. 676–681.

Derwent Abstract 24399 of Russian Patent 178771, Feb. 2, 1965, Pub. July 1966.

Derwent Abstract 39566 of Russian Patent 220920, July 1, 1967, Pub. Jan. 1969.

*Primary Examiner*—Lionel M. Shapiro
*Attorney, Agent, or Firm*—Behr & Woodbridge

[57] ABSTRACT

Lysozyme from human, avian, non-human mammalian, and vegatable sources is isolated from said sources and provided in a high degree of purity by adsorbing the lysozyme upon chitin obtained from *Loligo vulgaris* by contacting said chitin with an acidic aqueous suspension of the crude lysozyme containing material, and eluting the pure lysozyme from said chitin with aqueous acid.

19 Claims, No Drawings

METHOD OF ISOLATION OF LYSOZYME

FIELD OF THE INVENTION

Isolation of pure lysozyme.

BACKGROUND OF THE INVENTION

Lysozyme is a highly active enzyme which was originally isolated by Fleming during his early work on penicillin. Lysozyme is found in mammalian, including human, tissues and body fluids such as blood, tears, and milk as well as in avian sources, such as avian egg-white and vegetable sources. It is also found in bacteria and bacteriophages. The major sources of lysozyme to date has been avian eggs and various methods are known for the isolation thereof in reasonable degrees of purity. These procedures however are lengthy, tedious, and expensive and do not lend themselves readily to production scale isolation of lysozyme. Lysozyme from avian sources may be used as a food preservative. It has long been considered a highly desirable preservative since it may be passed into the human digestive system with no adverse effects thereto and does not suffer from the problem of chemical residue which effects many artificial preservatives. Unfortunately however the cost factor heretofore involved in producing large amounts of pure lysozyme have, in effect, prevented its large scale utilization for this highly desirable purpose.

Since lysozyme operates as a bacteriolytic agent it is of potential use as a potentiator for drugs such as antibiotics and the like. Unfortunately, heretofore there have been certain immunological barriers to its use for this purpose. While avian and non-human lysozyme may be ingested by humans without adverse immunological effects non-human lysozyme will set up antibody reactions when ininjected into the human circulatory system. When lysozyme from human sources is injected into the human circulatory system antibody response is sometimes obtained and sometimes not obtained. The only way of ensuring absolutely that no antibody response would be obtained would be to inject lysozyme obtained from the injected subject itself together with the desired drug. Thus, it would be desirable to develop a method for efficiently separating lysozyme from a human subject in such a way that the supplying constituents of that subject are not otherwise degraded. Similarly, since there are known tests for antibody response, if human lysozyme can be readily obtained from other human sources, it is a comparatively simple job of testing to determine whether or not a subject would exhibit antibody response if foreign human lysozyme were injected into that human system.

Heretofore the available methods of isolating lysozyme from human sources have not been sufficiently efficient either to supply an adequate amount of lysozyme in sufficient purity to ensure that no antibody response due to other protein sources would be invoked, or, the methods available for the supply of pure lysozyme have been so expensive as to be worthless from a practical, that is to say, nonacademic point of view.

Chitin is a known material which may be obtained from various marine sources such as crabs and the like. Chitin from crabs has been utilized in procedures for the isolation, but not purification, of lysozyme.

SUMMARY OF THE INVENTION

It has been found that chitin isolated from the squid (Loligo vulgaris) after being subjected to deamination provides an absorptive medium which specifically removes lysozyme from aqueous, slightly acid, suspensions containing same. The lysozyme may then be readily removed from the chitin by washing with aqueous dilute acid from which the lysozyme itself may be isolated by methods well known to the art. It is a specific advantage of this reaction that in one isolation step the concentration of lysozyme may be raised from about 1500 to 10,000 times.

It is a further advantage of this method that it is operative regardless of the source of lysozyme, that is to say, mammalian (human or non-human, avian or vegetable).

The lysozyme which is isolated by means of the preferred embodiments of the present invention is of high purity.

DESCRIPTION OF THE PREFERRED EMBODIMENTS

The process of the present invention can be conveniently divided into two parts. The first being the preparation of the absorption material and the second being the absorption procedure itself.

The chemical substance, chitin, which is utilized as the adsorbant material is found in many forms of marine life, such as the skeleton of arthropods, annelids, molusks medusoid coellenterates, in nematodes and achantocephalans. Only chitin isolated from the pens of the squid (*Loligo vulgaris*) was found suitable for use as a selective absorbant for lysozyme. While we do not wish to be bound by any theory, it is believed that this desirable property is due to the anti-parallel orientation of the chains of chitin in the physical form in which they are found. By anti-parallel is meant that the structural units are oriented parallel to each other but the directional sequence of the atoms in each structural unit alternates from one chain to the adjacent chain thereto.

The squid pens are removed from the animal and washed free of flesh, suitably with running tap water. The material is then dried overnight at moderately elevated temperature. Temperatures above 70°C but below 100°C, being suitable, 95°C being particularly desirable. The material is then cut into small pieces, suitably having dimensions in any direction of 1 centimeter or less and saline is added thereto. The purpose of the saline is to provide a suitable homogenization medium. The amount and concentration of saline is not critical, however, it has been found suitable to utilize from about 5 to about 20 suitably about 10 volumes of 0.1 to 5 normal, suitably about 1 normal aqueous sodium chloride. The mixture is then homogenized in a suitable rotating blade grinder at the highest speed available thereto. Homogenization is continued for from about 30 minutes to about 2 hours, suitably for about one hour, the mixture is removed from the homogenization unit, the supernatant liquid removed and discarded and made up once more to the original volume with more saline. It has been found desirable to sharpen the blades of the mixture between each homogenization step. This procedure is repeated from one to about five times, suitably 3 times. After discarding the last supernate, it is desirable to remove any residual fatty material. While any dilute water soluble acid may be utilized in this step, it has been found especially suitable to utilize water soluble organic acids and particular acetic acid in a strength of from about 0.5 to 2 suitably about 1 molar. The residual chitin is re-suspended in about 10 volumes of acid and homogenized once more for about one hour in the same or similar equipment. After homogenization the supernate is again discarded and the residual chitin is first dried, suitably at above 70°C but below 100°C preferably at about 95°C for a few hours, suitably overnight and pulverized, suitably in a ball mill to a powder of between 100 and 400 mesh. While any mesh in this range is suitable it has been found that chitin of approximately 100 mesh possesses the most desirable combination of available surface area, coupled with particulate size great enough to permit a good flow therethrough when used in a chromatographic column.

The chitin is then deaminated by any deamination method known to the art, it has been found particularly suitable to carry out the deamination by the Van Slyke procedure. The chitin is treated with nitrous acid to convert the amino groups thereon into hydroxy groups to yield desaminopolyhydroxy squid chitin. Any convenient source of nitrous acid may be employed, in the preferred procedure one part of chitin, 3 parts of glacial acetic acid and 9 parts of 30% aqueous sodium nitrite are agitated for about 24 hours. The thus treated material is then washed. In the preferred washing procedure the deaminated chitin is placed on a sintered glass filter, and washed with distilled water and suction until the effluent pH is above pH 5.5.

While any means of contacting the source of lysozyme with the squid chitin may be employed, it has been found must efficient to pack the chitin into a chromatographic column. It is preferred to prepare such chromatographic columns by gravity flow followed, preferably by washing with acetic acid, suitably with about 100 column volumes of acetic acid followed by distilled water until the pH of the effluent is again above pH 5.5.

PREPARATION OF LYSOZYME SOURCES FOR LYSOZYME EXTRACTION

While the preferred method of extracting lysozyme from its source is by chromatography through a chitin column it will be recognized that due to the diversity of the lysozyme sources somewhat different methods of pre-preparation have to be employed. It will be recognized that lysozyme constitutes a very small proportion of its source material which comprises to a greater or lesser extent, fibrous, particulate, or fatty materials. It will be understood that these and similar materials which constitute the major portion of the materials which contain lysozyme would seriously interfere with chromatographic extraction of lysozyme and must therefore be removed.

The basic principle in the following purification steps is the finding that the maximum aqueous solubility of lysozyme occurs between pH 3.8 and 4.6 and a pH of 4.5 is the most preferred. The methods of separation will of course depend on the nature of the source of material.

Where the source material is tissue material among which may be listed lung tissues, skin tissues, and, most suitable to all, placenta, tissues are cut into small pieces and homogenized in acidic solution preferably in a water soluble organic acid, most preferably .001M acetic acid in a conventional blender at high speed until complete disruption of the cells, followed by stirring in the cold (between about 0°C and about 5°C) for from about 5 to about 20, suitably from about 10 to about 21 days.

In the case of body fluids such as serum, plasma, saliva, or tears homogenization is not necessary. These fluids are diluted one-to-one with aqueous acid as above, suitably with 0.001M acetic acid, and is similarly stirred in the cold for from about 5 to about 20 days, suitably for about 10 days. Certain body fluids such as milk and colostrum have a high lipid content which must be removed. In these cases, the fluid is acidified to pH 4.5, suitably with 0.01M acetic acid and centrifuged. Three layers are noted, a top lipid layer, a central aqueous layer and a residue comprising denatured proteins and casein. Only the middle aqueous layer is utilized. Where the source of lysozyme is vegetables such as onions, radishes, papaya, and the like, these are processed in the same manner as tissues. Sources such as bacteriophage and certain bacteria, such as *Staphylococcus aureus*, *Streptococcus viridans* and *Streptococcus faecalis* which contain cellular material, are treated in the same manner as tissues.

Avian sources such as the egg-whites of hens, ducks, turkey, and fowls, are diluted 1:3 or 1:4 with 0.01M acetic acid with moderate stirring, the pH adjusted if necessary to pH 4.5, stood overnight at cold and centrifuged at high speed for the removal of particulate matter.

The aqueous acidic layers from each of the above sources contain the lysozyme dissolved therein but also contain fine particulate or pseudo-colloidal material which may very rapidly inactivate the chitin adsorbant. These aqueous layers are then centrifuged. Centrifugation may be for from about 1 hour at 8,000 g. to about 3 hours at 50,000 g. It has been found however that entirely satisfactory results are obtained by centrifugation for 2 hours at 30,000 g.

The aqueous supernate from this centrifugation is then contacted with the squid chitin.

ISOLATION OF LYSOZYME

While any mode of contacting the chitin with the lysozyme solution followed by removal of the lysozyme from the chitin may be used, the simplest and most effective mode is column chromatography wherein the aqueous acetic solution of the lysozyme is passed through a column of squid chitin and the lysozyme eluted therefrom with a suitable eluent.

In the preferred mode of carrying out the chromatography the lysozyme containing solution is charged to the squid chitin column through a delivery vessel at a controlled rate of flow. The optimum flow rate will of course depend on a number of factors, principally the mesh size of the chitin. However, it has been found that utilizing a chitin size of 100 mesh a flow rate of between 10 and 50 suitably 15 to 25 ml./cm squared of column cross-sectional area/per hour gives rise to suitable results. After passage of the lysozyme containing solution through the column the column is thoroughly washed with distilled water. The amount of wash is not critical however between about 8 and about 15 suitably about 12 column volumes of distilled water have been found satisfactory.

The lysozyme is then eluted with aqueous acid. There may be utilized mineral acids or water soluble organic acids. For example, there may be utilized dilute aqueous hydrochloric acid suitably of 2N strength or dilute aqueous sulfuric acid of .001 normal strength. There may also be used water soluble organic acids which may either be alkyl, aryl, aralkyl or alkaryl carboxylic acid. Especially preferred however are substantially volatile water soluble organic acids such as lower alkanoic acids having between 1 and 5 carbon atoms. It has been found especially suitable to utilize 0.01M acetic acid since not only is lysozyme readily soluble in this acid at this strength but the acid itself is sufficiently volatile to be readily removed by evaporation or lyophilization.

While other acids are operative it has been found that the highest yields at the highest purity have been obtained utilizing acetic acid. It has been found that the lysozyme is eluted in about 7 column volumes, the major portion being eluted in the second to fourth column volumes.

The course of the elution being followed by UV absorption at 280nm.

The lysozyme activity of each fraction is assayed by a modification of the method of Shugar (1951, Bull.Soc. Chim.Biol.33, 710 ) by recording the rate of lysis of a suspension of heat killed *Micrococcus lysodeikticus* (Sigma) (0.030 mg./100 ml. in 0.1M sodium phosphate buffer pH 7.00). A decrease in absorbancy of 0.001 per minute is taken as a unit of lysozyme activity.

The amount of protein is estimated according to the method of Lowry, Rosebrough, Farr and Randall (1951, J.Biol.Chem., 193, 265).

In a properly conducted isolation, a test of lysozyme activity in the effluent or in the washing shows 0(zero) biological activity against the micrococcal suspension. With the application of the eluent, the lysozyme is eluted with a recovery greater than 99%.

The eluted lyzosyme is concentrated first by flash evaporation, or under reduced pressure. If the eluate is not yet homogeneous, it is heated for 1–2 minutes at 100°C on a water bath, centrifuged for 1–2 hours at high speed for the removal of the denatured material, and the supernate brought to dryness by flash evaporation under reduced pressure of lyophylization.

The purity of this product was tested by disc gel electrophoresis as well as isoelectric focusing. These tests all showed a single band of protein moving with the same velocity as purified hen egg-white lysozyme which has been used as a control.

Immunological analysis was carried out upon the purified lysozyme obtained from different human tissues from different subjects by injecting the lysozyme into different rabbits and assaying the antibodies thus generated. The results obtained indicate prima facie that immunologically, though not necessarily chemically, all the human lysozymes tested appear to be identical.

The results obtained in the isolation of lysozymes from different sources by the method of the present invention are summarized in the tables below.

EXAMPLE I

CHITIN STRUCTURAL UNIT

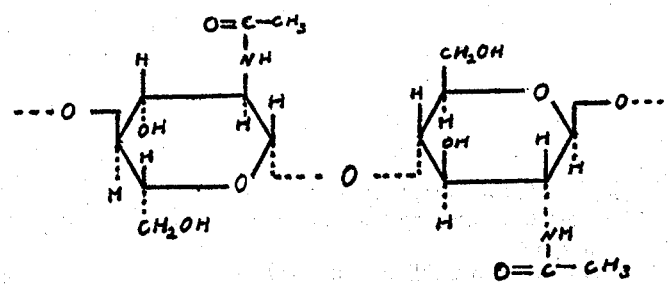

HUMAN LUNG LYSOZYME

ISOLATION BY AFFINITY CHROMATOGRAPHY ON DEAMINATED CHITIN.

Column: diameter 12 mm; height 295 mm; bed volume 33.3 ml; grain 200–400 mesh.

Adsorption washings and elution at constant flow rate 20 cc/hour.

Washed with distilled water pH 6.5; Eluted with 0.01M acetic acid.

| Fraction | ml | Lysozyme Units | Proteins ng. | Specific Activity Units/ng | Purification Sp.Act/Sp.Act in homogenate |
|---|---|---|---|---|---|
| Lung homogenate | 100 | 3,700 | 3,250,000 | 0.001138 | 1 |
| Filtrate | 100 | 0 | 3,180,000 | | |
| Wash | 1,050 | 0 | 66,050 | | |
| Recovery in Lysozyme Inactive Fractions | 1,150 | 0 | 3,246,050 | | |
| % | | 0 | 99.89 | | |
| Eluate No. 1 | 10 | 200 | 160 | 1.250000 | 1,098 |
| 2 | 10 | 370 | 300 | 1.233333 | 1,084 |
| 3 | 10 | 540 | 430 | 1.255814 | 1,106 |
| 4 | 10 | 690 | 550 | 1.254545 | 1,102 |
| 5 | 10 | 840 | 680 | 1.235529 | 1,086 |
| 6 | 10 | 610 | 480 | 1.270833 | 1,117 |
| 7 | 10 | 320 | 250 | 1.280000 | 1,125 |
| 8 | 10 | 120 | 120 | 1.200000 | 1,054 |
| Recovery in Lysozyme Active Fractions | 80 | 3,690 | 2,960 | | |
| % | | 99.73 | 0.0009 | | |
| AVERAGE ENRICHMENT IN LYSOZYME × 1,097 | | | | | |

EXAMPLE II

HUMAN SKIN LYSOZYME
ISOLATION BY AFFINITY CHROMATOGRAPHY ON DEAMINATED CHITIN.

Column: diameter 12 mm; bed height 425 mm.; bed volume 48.0 ml. DeCh grain size: 200–400 mesh Adsorption, washing and elution at constant flow of 16 cc/hour.

Washing with distilled water (pH 6.4). Eluant 0.001 M AcOH

| Fraction | ml | Lysozyme Units | Proteins ng | Specific Activity Unit/ng | Purification Sp.Act/Sp.Act in homogenate |
|---|---|---|---|---|---|
| Skin homogenate | 400 | 2,000 | 12,800,000 | 0.000156 | 1 |
| Filtrate | 400 | 0 | 12,400,000 | | |
| Wash | 1,020 | 0 | 350,020 | | |
| Eluate No. 1 | 12.5 | 375 | 275 | 1.363636 | 8,741 |
| 2 | 12.5 | 750 | 538 | 1.395349 | 8,94 |
| 3 | 12.5 | 500 | 375 | 1.333333 | 8,947 |
| 4 | 12.5 | 250 | 188 | 1.333333 | 8,547 |
| 5 | 12.5 | 125 | 125 | 1.428571 | 9,158 |
| Recovery: | | | | | |
| In Lysozyme inactive fractions | | 0 | 12,750,020 (99.61%) | | |
| In Lysozyme active fractions | | 2,000 (100%) | 1,501 (0.0001%) | | |
| AVERAGE ENRICHMENT IN LYSOZYME × 8788 | | | | | |

EXAMPLE III

HUMAN PLASMA LYSOZYME
ISOLATION BY AFFINITY CHROMATOGRAPHY ON DEAMINATED CHITIN.

Column: diameter 12 mm; DeCh height 275 mm; bed volume 31.1 ml.; DeCh grain size: 200–400 mesh.

Adsorption, washings and elution at constant flow rate of 18 cc/hour.

Washings with distilled water, pH 6.6; elution with 0.01M AcOH

| Fraction | ml. | Lysozyme Units | Proteins ng | Specific Activity Units/ng | Purification Sp.Act/Sp.Act in homogenate |
|---|---|---|---|---|---|
| Plasma homogenate | 250 | 9,000 | 13,725,000 | 0.000650 | 1 |
| Filtrate | 250 | 0 | 13,700,000 | | |
| Washings | 1,260 | 0 | 12,600 | | |
| Eluate No. 1 | 15 | 1,650 | 1,500 | 1.500000 | 2,308 |
| 2 | 15 | 4,350 | 3,750 | 1.380950 | 2,125 |
| 3 | 15 | 2,100 | 1,400 | 1.400000 | 2,154 |
| 4 | 15 | 750 | 600 | 1.250000 | 1,923 |
| 5 | 15 | 150 | 110 | 1.363636 | 2,098 |
| Recovery: | | | | | |
| In Lysozyme inactive fractions | | 0 U (0%) | 13,721,000 ng (99.91%) | | |
| In Lysozyme active fractions | | 9,000 U (100%) | 6,860 ng (0.005%) | | |
| AVERAGE ENRICHMENT IN LYSOZYME × 2,122 | | | | | |

EXAMPLE IV

HUMAN SERUM LYSOZYME
ISOLATION BY AFFINITY CHROMATOGRAPHY ON DEAMINATED CHITIN

Column: diameter 10 mm; height 135 mm; bed volume 10.9 ml. grain size: 200–400 mesh.

Adsorption, wash and elution at constant flow rate: 18 cc/hour.

Washed with distilled water (pH 6.5), eluted with 0.01M acetic acid.

| Fraction | ml. | Lysozyme Units | Proteins ng | Specific Activity Units/ng | Purification Sp.Act/Sp.Act in homogenate |
|---|---|---|---|---|---|
| Homogenate | 100 | 1,200 | 5,732,000 | 0.000209 | 1 |
| Filtrate | 100 | 0 | 5,620,000 | | |
| Wash | 1,100 | 0 | 98,100 | | |
| Recovery in Lysozyme Inactive fractions | 1,200 | 0 | 5,718,100 | | |
| % | | 0 | 99.76 | | |
| Eluate No. 1 | 10 | 90 | 80 | 1.125000 | 5,372 |
| 2 | 10 | 300 | 240 | 1.250000 | 5,969 |
| 3 | 10 | 500 | 380 | 1.315779 | 6,296 |
| 4 | 10 | 260 | 220 | 1.181818 | 5,644 |
| 5 | 10 | 50 | 40 | 1.250000 | 5,969 |
| Recovery in Lysozyme Active fractions | 50 | 1,200 | 960 | | |
| % | | 100 | 0.02 | | |
| AVERAGE ENRICHMENT IN LYSOZYME × 5,850 | | | | | |

EXAMPLE V

HUMAN PLACENTA LYSOZYME

ISOLATION BY AFFINITY CHROMATOGRAPHY ON DEAMINATED CHITIN.

Column: diameter 12 mm; height 435 mm; bed volume 49.2 ml. grain size: 200–400 mesh.

Adsorption, washings and elution at constant flow: 20 cc/hour.

Washed with distilled water, eluted with 0.01M acetic acid.

EXAMPLE VI

HUMAN MONOCYTIC LYSOZYME

ISOLATION BY AFFINITY CHROMATOGRAPHY ON DEAMINATED CHITIN.

Column: diameter 12 mm; height 425 mm; bed volume 48.0 ml; grain size: 200–400 mesh.

Adsorption, washing and elution at constant flow: 16 cc/hour.

Washed with distilled water (pH 6.5), eluted with 0.01M acetic acid.

| Fraction | ml. | Lysozyme Units | Proteins ng | Specific Activity Units/ng | Purification Sp.Act/Sp.Act in homogenate |
|---|---|---|---|---|---|
| Homogenate | 200 | 3,000 | 11,840,000 | 0.000253 | 1 |
| Filtrate | 200 | 0 | 11,760,000 | | |
| Wash | 1,000 | 0 | 975,000 | | |
| Recovery in Lysozyme Inactive fractions | 1,200 | 0 | 11,835,000 | | |
| % | | 0 | 99.96 | | |
| Eluate No. 1 | 10 | 250 | 210 | 1.190476 | 4,705 |
| 2 | 10 | 700 | 550 | 1.272727 | 5,031 |
| 3 | 10 | 900 | 700 | 1.285714 | 5,082 |
| 4 | 10 | 700 | 550 | 1.272727 | 5,031 |
| 5 | 10 | 300 | 240 | 1.250000 | 4,941 |
| 6 | 10 | 100 | 80 | 1.250000 | 4,941 |
| 7 | 10 | 40 | 30 | 1.333333 | 5,270 |
| Recovery in Lysozyme Active fractions | 70 | 2,990 | 2,360 | | |
| % | | 99.67 | 0.02 | | |
| AVERAGE ENRICHMENT IN LYSOZYME × 5,000 | | | | | |

5 ml. Human Monocytes obtained by the Method of Archer and Kooptzoff (1958) were homogenized by sonication in 45 ml. Acetic acid 0.001M, then stirred at 4°C for 12 days prior to the application to the column.

| Fraction | ml. | Lysozyme Units | Proteins ng | Specific Activity Units/ng | Purification Sp.Act/Sp.Act in homogenate |
|---|---|---|---|---|---|
| Homogenate | 50 | 600 | 1,196,000 | 0.000501 | 1 |
| Filtrate | 50 | 0 | 1,192,000 | | |
| Wash | 204 | 0 | 3,604 | | |
| Recovery in Lysozyme Inactive fractions | 254 | 0 | 1,195,604 | | |
| % | | 0 | 99.98 | | |
| Eluate No.1 | 4 | 44 | 32 | 1.375000 | 2,739 |
| 2 | 4 | 88 | 68 | 1.294110 | 2,578 |
| 3 | 4 | 128 | 92 | 1.391304 | 2,772 |
| 4 | 4 | 180 | 130 | 1.384615 | 2,764 |

-continued

| Fraction | ml. | Lysozyme Units | Proteins ng | Specific Activity Units/ng | Purification Sp.Act/Sp.Act in homogenate |
|---|---|---|---|---|---|
| 5 | 4 | 108 | 76 | 1.421053 | 2,831 |
| 6 | 4 | 44 | 32 | 1.375000 | 2,739 |
| 7 | 4 | 8 | 15 | 1.333333 | 2,656 |
| Recovery in Lysozyme Active fractions | 28 | 600 | 432 | | |
| % | | 100 | 0.0004 | | |
| AVERAGE ENRICHMENT IN LYSOZYME × 2,726 | | | | | |

EXAMPLE VII

HUMAN MILK LYSOZYME

ISOLATION BY AFFINITY CHROMATOGRAPHY ON DEAMINATED CHITIN.

Column: diameter 14 mm; height 444 mm; bed volume 68.3ml; grain 200–400 mesh.

Adsorption, washings and elution at constant flow rate: 20 cc/hour.

Washed with distilled water (pH 6.6), elution with 0.01M acetic acid.

| Fraction | ml. | Lysozyme Units | Proteins ng. | Specific Activity Units/ng | Purification Ap.Act/Sp.Act in whey |
|---|---|---|---|---|---|
| Milk whey | 100 | 7,600 | 3,320,000 | 0.002289 | 1 |
| Filtrate | 100 | 0 | 3,300,000 | | |
| Wash | 1,000 | 0 | 13,600 | | |
| Recovery in Lysozyme Inactive fractions | 1,100 | 0 | 3,313,600 | | |
| % | | 0 | 99.81 | | |
| Eluate No.1 | 10 | 480 | 400 | 1.200000 | 524 |
| 2 | 10 | 1,590 | 1,200 | 1.325000 | 579 |
| 3 | 10 | 2,400 | 1,800 | 1.333333 | 582 |
| 4 | 10 | 2,040 | 1,500 | 1.360000 | 594 |
| 5 | 10 | 720 | 520 | 1.384615 | 605 |
| 6 | 10 | 370 | 280 | 1.321429 | 577 |
| Recovery in Lysozyme Active fractions | 60 | 7,600 | 5,700 | | |
| % | | 100 | 0.002 | | |
| AVERAGE ENRICHMENT IN LYSOZYME × 577 | | | | | |

EXAMPLE VIII

HUMAN SALIVA LYSOZYME

ISOLATION BY AFFINITY CHROMATOGRAPHY ON DEAMINATED CHITIN.

Column: diameter 10 mm; height 252 mm; bed volume 19.8 ml; grain 200–400 mesh.

Adsorption, washings and elution at constant flow rate: 16 cc/hour.

Washed with distilled water (pH 6.6), eluted with 0.01M acetic acid.

| Fraction | ml. | Lysozyme Units | Proteins ng | Specific Activity Units/ng | Purification Sp.Act/Sp.Act in homogenate |
|---|---|---|---|---|---|
| Saliva homogenate | 50 | 2,600 | 184,000 | 0.001413 | 1 |
| Filtrate | 50 | 0 | 180,000 | | |
| Wash | 520 | 0 | 2,520 | | |
| Recovery in Lysozyme Inactive fractions | 570 | 0 | 182,520 | | |
| % | | 0 | 99.2 | | |
| Eluate No.1 | 10 | 700 | 520 | 1.296296 | 917 |
| 2 | 10 | 1,100 | 810 | 1.358024 | 961 |
| 3 | 10 | 510 | 400 | 1.275000 | 902 |
| 4 | 10 | 200 | 160 | 1.250000 | 885 |
| 5 | 10 | 80 | 60 | 1.333333 | 944 |
| Recovery in Lysozyme Active fractions | 50 | 2,590 | 1,950 | | |
| % | | 99.62 | 0.01 | | |
| AVERAGE ENRICHMENT IN LYSOZYME × 922 | | | | | |

EXAMPLE IX

HUMAN EOSINOPHYLIC LYSOZYME

ISOLATION BY AFFINITY CHROMATOGRAPHY ON DEAMINATED CHITIN.

Column: diameter 12 mm; height 425 mm; bed volume 48.0ml; grain size: 200–400 mesh.

Adsorption, washing and elution at constant flow: 16 cc/hour.

Washed with distilled water (pH 6.5), eluted with 0.01M acetic acid.

5 ml. Eosynophiles, obtained from human blood by the method of Lindgreen (1958), were homogenized by sonication in 25 ml. Acetic acid 0.001M, stirred for 10 days at 4°C, centrifuged and applied to the column.

| Fraction | ml. | Lysozyme Units | Proteins ng | Specific Activity Units/ng | Purification Sp.Act/Sp.Act in homogenate |
|---|---|---|---|---|---|
| Homogenate | 30 | 180 | 1,050,000 | 0.000171 | 1 |
| Filtrate | 30 | 0 | 1,047,000 | | |
| Wash | 100 | 0 | 2,700 | | |
| Lysozyme Inactive fractions | 130 | 0 | 1,049,700 | (99.97%) | |
| Eluate No.1 | 5 | 45 | 35 | 1.285714 | 7,519 |
| 2 | 5 | 100 | 75 | 1.333333 | 7,797 |
| 3 | 5 | 25 | 20 | 1.250000 | 7,310 |
| 4 | 5 | 10 | 75 | 1.333333 | 7,797 |
| In Lysozyme Active fractions | 20 | 180(100%) | 1,375 | (0.008%) | |

AVERAGE ENRICHMENT IN LYSOZYME × 7,606

EXAMPLE X

HUMAN KIDNEY LYSOZYME

ISOLATION BY AFFINITY CHROMATOGRAPHY ON DEAMINATED CHITIN.

Column: diameter 12 mm; height 295 mm; bed volume 33.3 ml; grain: 200–400 mesh.

Adsorption, washings and elution at constant flow rate: 18 cc/hour.

Washed with distilled water (pH 6.6), eluted with 0.01M acetic acid.

| Fraction | ml. | Lysozyme Units | Proteins ng | Specific Activity Units/ng | Purification Sp.Act/Sp.Act in homogenate |
|---|---|---|---|---|---|
| Kidney Homogenate | 100 | 4,200 | 4,355,000 | 0.000964 | 1 |
| Filtrate | 100 | 0 | 4,310,000 | | |
| Wash | 1,020 | 0 | 40,020 | | |
| Recovery In Lysozyme Inactive fractions | 1,120 | 0 | 4,350,020 | | |
| % | 100 | 0 | 99.89 | | |
| Eluate No.1 | 10 | 450 | 320 | 1.437500 | 1,491 |
| 2 | 10 | 810 | 570 | 1.421053 | 1,474 |
| 3 | 10 | 900 | 640 | 1.406250 | 1,459 |
| 4 | 10 | 830 | 590 | 1.406780 | 1,459 |
| 5 | 10 | 670 | 460 | 1.456622 | 1,511 |
| 6 | 10 | 360 | 250 | 1.440000 | 1,494 |
| 7 | 10 | 160 | 120 | 1.333333 | 1,383 |
| Recovery In Lysozyme Active fractions | 70 | 4,190 | 2,950 | | |
| % | 100 | 99.76 | 0.068 | | |

AVERAGE ENRICHMENT IN LYSOZYME × 1467

EXAMPLE XI

ISOLATION OF RABBIT LUNG LYSOZYME BY AFFINITY CHROMATOGRAPHY ON DEAMINATED CHITIN.

Column: diameter 12 mm; bed height 160/180 mm; bed volume 22 ml; grain: 100 mesh Adsorption, washings and elution at constant flow rate: 16 cc/hour.

Washed with distilled water (pH 6.5), eluted with 0.1M acetic acid.

| Fraction | ml. | Lysozyme Units | Protein ng | Specific Activity | Purification |
|---|---|---|---|---|---|
| Rabbit Lung homogenate | 298 | 6,450 | 5,849,740 | 0.000110 | 1 |
| Filtrate | 298 | 0 | 5,807,420 | 0 | |
| Wash | 3,400 | 0 | 41,600 | 0 | |
| Eluted with 0.1 Acetic acid | 450 | 6,430 | 580 | 11,086207 | 10,078 times |
| Recovery % | 99.7 | | | | |

EXAMPLE XII

ISOLATION OF COW LUNG LYSOZYME BY AFFINITY CHROMATOGRAPHY ON DEAMINATED CHITIN.

Column: diameter 12 mm; bed height 160/180 mm; bed volume 22 ml; grain: 100 mesh.

Adsorption, washing and elution at constant flow rate: 16 cc/hour.

Washed with distilled water (pH 6.5), eluted with 0.1M acetic acid

| Fraction | ml. | Lysozyme Units | Proteins ng | Specific Activity | Purification |
|---|---|---|---|---|---|
| Cow Lung homogenate | 195 | 4,350 | 8,405,720 | 0.000518 | 1 |
| Filtrate | 195 | 0 | 8,225,000 | 0 | |
| Wash | 2,250 | 0 | 180,500 | 0 | |
| Elution | 350 | 4,340 | 220 | 19,72773 | 3,808 |
| Recovery % | | 99.77 | | | |

EXAMPLE XIII

ISOLATION OF LETTUCE LYSOZYME BY AFFINITY CHROMATOGRAPHY ON DEAMINATED CHITIN.

Column: diameter 12 mm; bed height 160/180 mm; bed volume 22 ml; grain: 100 mesh.

Adsorption, washings and elution at constant flow rate: 16 cc/hour.

Washed with distilled water (pH 6.5), eluted with 0.1M acetic acid.

| Fraction | ml. | Lysozyme Units | Proteins ng | Specific Activity | Purification |
|---|---|---|---|---|---|
| Homogenate | 250 | 750 | 352,000 | 0,002131 | 1 |
| Filtrate | 250 | 0 | 341,000 | 0 | |
| Wash | 1,500 | 0 | 10,750 | 0 | |
| Eluate | 250 | 745 | 250 | 1,000,000 | 470 |
| Recovery % | 99.33% | | | | |

We claim:

1. A method of isolating lysozyme from a source thereof comprising:
   a. treating an aqueous suspension of said lysozyme containing source material with deaminated squid chitin,
   b. separating the chitin from said suspension, washing said chitin with aqueous acid and separating said aqueous acid from said chitin.

2. A process according to claim 1 additionally comprising removing the lysozyme from said acid wash.

3. A method according to claim 1 wherein the chitin is obtained by the successive steps of:
   a. homogenizing dried, flesh-free pens of the squid, Loligo vulgaris in aqueous saline,
   b. discarding the aqueous supernate,
   c. resuspending the residual material in dilute aqueous organic acid and rehomogenizing,
   d. discarding the aqueous supernate,
   e. drying the residue designated as chitin,
   f. powdering the chitin to pass through a mesh of 100 to 400 mesh size,
   g. reacting the chitin with nitrous acid.

4. A process according to claim 3 wherein the source of nitrous acid is sodium nitrite in the presence of an acid.

5. A process according to claim 4 wherein the acid is glacial acetic acid.

6. A process according to claim 1 which comprises additionally suspending lysozyme containing material in an aqueous medium of pH between 3.8 and 4.6 and separating therefrom the water insoluble material, before treating said lysozyme suspension with chitin.

7. A process according to claim 6 wherein the suspending step comprises homogenizing the lysozyme containing material in dilute aqueous acid, separating the aqueous solution from other fractions present and preserving said aqueous fractions.

8. A process according to claim 6 wherein the separation step comprises centrifuging and preserving the aqueous portion.

9. A process according to claim 6 which comprises:
   a. charging the deaminated chitin to a chromatograhic column,
   b. charging the aqueous solution containing lysozyme to said column,
   c. eluting said column with aqeuous acid.

10. A process according to claim 9 additionally comprising the step of washing said column with water prior to elution with aqueous acid.

11. A process according to claim 9 additionally comprising separating the lysozyme from the acidic eluate.

12. A process according to claim 11 wherein the acid is a substantially volatile water soluble organic acid.

13. A process according to claim 9 wherein the lysozyme source material is human tissues.

14. A process according to claim 9 wherein the lysozyme source material is human placenta.

15. A process according to claim 9 wherein the lysozyme source material is human plasma.

16. A process according to claim 9 wherein the lysozyme source material is avian egg-white.

17. A process according to claim 9 wherein the lysozyme source material is mammalian milk.

18. A process according to claim 9 wherein the lysozyme source material is mammalian blood.

19. A process according to claim 9 wherein the lysozyme source material is vegetables.

* * * * *